US00PP16602P3

(12) United States Plant Patent
Lim et al.

(10) Patent No.: US PP16,602 P3
(45) Date of Patent: May 30, 2006

(54) SHRUB ROSE PLANT NAMED 'BAIPOME'

(50) Latin Name: *Rosa hybrida*
Varietal Denomination: BAIpome

(75) Inventors: Peter P. Lim, Yamhill, OR (US); Martin Nemko, Oakland, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 106 days.

(21) Appl. No.: 10/772,244

(22) Filed: Feb. 6, 2004

(65) Prior Publication Data

US 2005/0177906 P1 Aug. 11, 2005

(51) Int. Cl.
*A01H 5/00* (2006.01)

(52) U.S. Cl. ..... Plt./102
(58) Field of Classification Search ..... Plt./102, Plt./107
See application file for complete search history.

(56) References Cited

U.S. PATENT DOCUMENTS

PP7,282 P * 7/1990 Noack ..... Plt./101
PP15,070 P2 * 8/2004 Montesino ..... Plt./107
PP15,287 P2 * 11/2004 Warner ..... Plt./102

OTHER PUBLICATIONS

Tess U.S. Trademark Appliation Ser. No. 76485001 'Garden Path'.*

* cited by examiner

*Primary Examiner*—Kent Bell
*Assistant Examiner*—W. C. Haas
(74) *Attorney, Agent, or Firm*—Buchanan Ingersoll PC

(57) ABSTRACT

A new and distinct variety of landscape shrub rose plant is provided which abundantly forms on a continuous basis single cup-shaped light soft pink blossoms having a white center. The plant exhibits a compact, tight, and rounded growth habit, glossy medium green foliage, and excellent tolerance to Black Spot and Powdery Mildew. The attractive medium green glossy foliage contrasts nicely with the light blossom coloration. A tough rose plant of small stature and good hardiness is provided. The plant can be grown to advantage as a specimen, border planting, or as a mass planting.

1 Drawing Sheet

Botanical designation: *Rosa hybrida.*
Varietal denomination: 'BAIpome'.

SUMMARY OF THE INVENTION

The new variety of *Rosa hybrida* landscape shrub rose plant was created at Yamhill, Oreg. during 1995 by artificial pollination wherein two parents were crossed which previously had been studied in the hope that they would contribute the desired characteristics. The female parent (i.e., the seed parent) was the 'Noatraum' variety U.S. Plant Pat. No. 7,282). The male parent (i.e., the pollen parent) also was the 'Noatraum' variety. The parentage of the new variety can be summarized as follows:

'Noatraum'×'Noatraum'.

The seeds resulting from the above pollination were sown and plants were obtained which were physically and biologically different from each other. Selective study resulted in the identification during 1998 of a single plant of the new variety having the distinctive ornamental characteristics hereafter described.

It was found that the new variety of the present invention:

(a) exhibits a compact, tight, and rounded growth habit, (b) abundantly forms on a continuous basis in clusters attractive single cup-shaped light soft pink blossoms having a white center, (c) forms glossy medium green adult foliage, (d) displays excellent tolerance to Black Spot and Powdery Mildew; and (e) is particularly well suited for growing as attractive ornamentation in parks and gardens.

The young rose pink flower buds open to the light pink blossoms having a white center that cover the bush throughout the season. The aging petals commonly detach cleanly and do not detract from the attractiveness of the blooms. A tough shrub rose plant having good hardiness is provided.

The new variety is a small stature versatile landscape plant that well meets the needs of the horticultural industry. It can be grown to advantage anywhere in the landscape where attractive ornamentation is desired. The distinctive blossoms are displayed throughout the season. The plant can be grown as a specimen, border planting, or as a mass ground cover.

The new variety can be readily distinguished from other varieties including its parental 'Noatraum' variety. More specifically, the 'Noatraum' variety forms much darker pink blossoms with near white centers.

The new variety has been found to undergo asexual propagation by budding on an understock and by the rooting of cuttings. 'Dr. Huey' rootstock (non-patented in the United States) was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated '95K61-1P'. The new variety subsequently has been named the 'BAIpome' variety, and currently is being marketed while using the PINK GNOME and GARDEN PATH trademarks.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by the rooting of cuttings, were approximately two and three years of age, and were being grown outdoors at St. Paul, Minn. and at Yamhill, Oreg.

DETAILED DESCRIPTION

Figure 1:
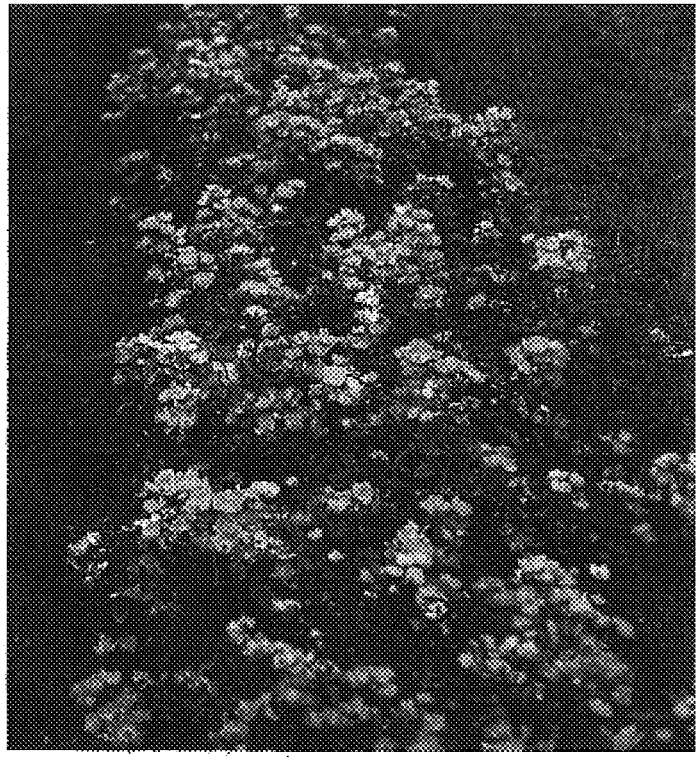
FIG. 1 illustrates typical plants with blossoms in various stages of opening and foliage of the new variety. Clusters of the attractive single cup-shaped soft pink blossoms with white centers are shown.
Figure 2:
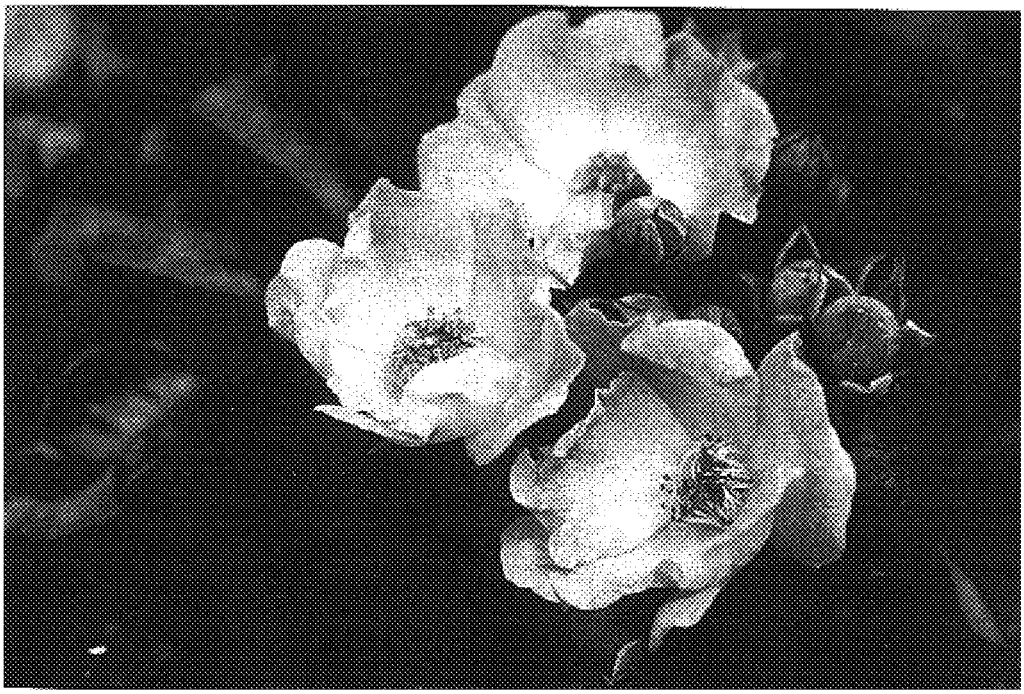
FIG. 2 illustrates a close view of typical buds and fully open flowers of the new variety in greater detail.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2002 and 2003 at St. Paul, Minn., and July 2003 at Yamhill, Oreg.

Botanical classification: *Rosa hybrida,* var. 'BAIpome'.
Class: Landscape Shrub.
Plant:
- *Height.*—Approximately 30 cm on average at the end of the growing season.
- *Width.*—Approximately 50 cm on average at the end of the growing season.
- *Habit.*—Compact, tight, and rounded.

Branches:
- *Color.*—Young stems: Green Group 138B with highlights of Greyed-Purple Group 183C. Adult wood: commonly between Green Group 137B and 137C. Internode length: approximately 1.8 mm on average. Internode diameter: approximately 3.1 mm on average. Internode distance: approximately 1.8 mm on average between internodes.
- *Thorns.*—Size: commonly approximately 0.4 cm in length on average with prickles on the younger stems. Color: commonly between Greyed-Purple Group 187B and 187C.

Leaves:
- *Size.*—Approximately 6.2 cm in length on average and approximately 5.1 cm in width on average.
- *Stiples.*—Two per leaf, generally parallel with the auricle facing outward, approximately 6.7 mm in length on average, approximately 4.0 mm in width on average, Yellow-Green Group 144A in coloration with stripes and solid areas of Green Group 137B and Greyed-Red Group 182A at the middle ridge.
- *Petioles.*—Upper surface: Green Group 137B with a center valley of Green Group 138C. Under surface: Green Group 138B. Length: approximately 1.7 cm on average. Diameter: Approximately 2 mm on average.
- *Rachis.*—Length: approximately 3.6 cm on average. Diameter: approximately 0.85 mm on average.
- *Leaflets.*—Number: 3, 5 (most often), and 7, per compound leaf. Shape: ovate with a rounded base and an acuminate tip. Serration: serrulate. Texture: bears a glossy finish and is physically firm. General appearance: medium green with a glossy surface when mature. Color (young foliage): Upper surface: Green Group 137B. Under surface: Green Group 137C. Color (adult foliage): Upper surface: Green Group 137B and 137C. Under surface: commonly between Green Group 137D and 138B.

Inflorescence:
- *Number of flowers.*—Commonly approximately 18 blooms on average per cluster on a lateral stem.
- *Peduncle.*—Yellow-Green Group 144A with highlights of Red-Purple Group 59A in coloration, the length is approximately 1.85 cm on average, and the diameter is approximately 1.3 mm on average.
- *Sepals.*—Upper surface: Yellow-Green Group 146B fading at the margin to Yellow-Green Group 144C. Under surface: Yellow-Green Group 146C fading at the margin to Yellow-Green Group 145C. Number: 5. Size: approximately 6.7 mm in length on average and approximately 4.1 mm in width on average at the widest point. Margin: entire with a ciliate fringe of short hairs.
- *Buds.*—Shape: generally rounded. Size: small. Length: approximately 0.75 cm on average. Diameter: Approximately 0.75 cm on average. Color: Upper surface: commonly between Red-Purple Group 58C and 58D fading to Yellow Group 2B at the base. Under surface: Red-Purple Group 58C with some Red-Purple Group 62A particularly at the veins.
- *Flower.*—Form: single. Shape: as a shallow cup, generally round, loosely circular and somewhat informal. The petal shape and ruffled petal margins sometimes impart an unbalanced and somewhat irregular appearance to the flowers. Diameter: approximately 2 cm on average. Depth: approximately 1.5 cm on average. Color (when opening begins): Upper surface: between Red-Purple Group 62A and 62B with highlights of Red-Purple Group 63C at the margin. Under surface: Red-Purple Group 62A with highlights of Red-Purple Group 63C. Color (when blooming): Upper surface: Red-Purple Group 62B blending to White Group 155C at the center. Under surface: Red-Purple Group 62C blending to White Group 155D at the center. Color (at end of blooming): Upper surface: Red-Purple Group 62D over approximately 65 percent of the surface and blending to White Group 155D at the center. Under surface: Red-Purple Group 62D over approximately 65 percent of the surface and blending to White Group 155D at the center. Color (basal petal spot): White Group 155A. Fragrance: slight green apple. Lasting quality: the blossoms commonly last approximately 5 to 7 days on average depending upon the temperature and sunlight exposure. Petal number: 5 under normal growing conditions. Petal shape: heart-shaped, with an emarginated tip and a rounded base. Petal margins: ruffled. Petal drop: commonly the petals detach cleanly at full blossom maturity. Anthers: Greyed-Orange Group 163B in coloration. Filament number: commonly approximately 58 on average. Filament color: Greyed-Yellow Group 162A in coloration. Pistils: approximately 20 on average. Stigmas: Yellow-Green Group 150A in coloration. Styles: Yellow Group 7A in coloration. Receptacle: separate and free. Hip color: Greyed-Red Group 178B suffused with Yellow-Green Group 146B at maturity. Hip shape: oval. Hip length: approximately 4.5 mm on average. Hip width: approximately 4.1 mm on average. Seeds:

medium beige in coloration, approximately 4.0 mm in length, and number approximately 21 per hip on average.

Development:

*Vegetation.*—Vigorous, and compact.

*Blooming.*—Abundant and continuous throughout the season.

*Resistance to diseases.*—Excellent tolerance to Black Spot, and Powdery Mildew.

*Hardiness zone.*—U.S.D.A. Hardiness Zone Nos. 4 to 9.

I claim:

1. A new and distinct variety of landscape shrub rose plant characterized by the following combination of characteristics:

(a) exhibits a compact, tight, and rounded growth habit, (b) abundantly forms on a continuous basis in clusters attractive single cup-shaped light soft pink blossoms having a white center.

(c) forms glossy medium green adult foliage, (d) displays excellent tolerance to Black Spot and Powdery Mildew, and (e) is particularly well suited for growing as attractive ornamentation in parks and gardens;

substantially as herein shown and described.

* * * * *